United States Patent [19]

Strohmaier

[11] Patent Number: 5,338,194
[45] Date of Patent: Aug. 16, 1994

[54] MEDICAL TREATMENT DEVICE AND METHOD FOR CLEANING A FLEXIBLE TUBE LINE

[75] Inventor: Ernst Strohmaier, Bad Schussenried, Fed. Rep. of Germany

[73] Assignee: Kaltenbach & Voigt GmbH & Co., Biberach/Riss, Fed. Rep. of Germany

[21] Appl. No.: 981,508

[22] Filed: Nov. 25, 1992

[30] Foreign Application Priority Data

Nov. 25, 1992 [DE] Fed. Rep. of Germany ....... 4138672

[51] Int. Cl.$^5$ .............................................. A61C 1/10
[52] U.S. Cl. .......................................... 433/82; 433/84; 604/27
[58] Field of Search ...................... 433/82, 84, 85, 86, 433/88; 604/27, 28; 128/66

[56] References Cited

U.S. PATENT DOCUMENTS 3,213,537 10/1965 Balamuth et al. .................... 433/86
5,044,952 9/1991 Castellini .............................. 433/84

FOREIGN PATENT DOCUMENTS

WO88/02621 4/1988 World Int. Prop. O. .

Primary Examiner—John J. Wilson
Attorney, Agent, or Firm—Scully, Scott, Murphy & Presser

[57] ABSTRACT

A medical treatment device, in particular for surgical purposes, consisting of a treatment instrument in the form of a handpiece which is connected to a control unit through a supply line. Operatively associated therewith, and preferably with the control unit, is a media source which supplies cooling fluid and to which the supply line is connected with a flexible line extending either thereon or within. Associated therewith is a rinsing device possessing a rinsing agent source and a collecting container, which device can be selectively connected to the flexible line. Also disclosed is a method for cleaning the flexible line.

12 Claims, 5 Drawing Sheets

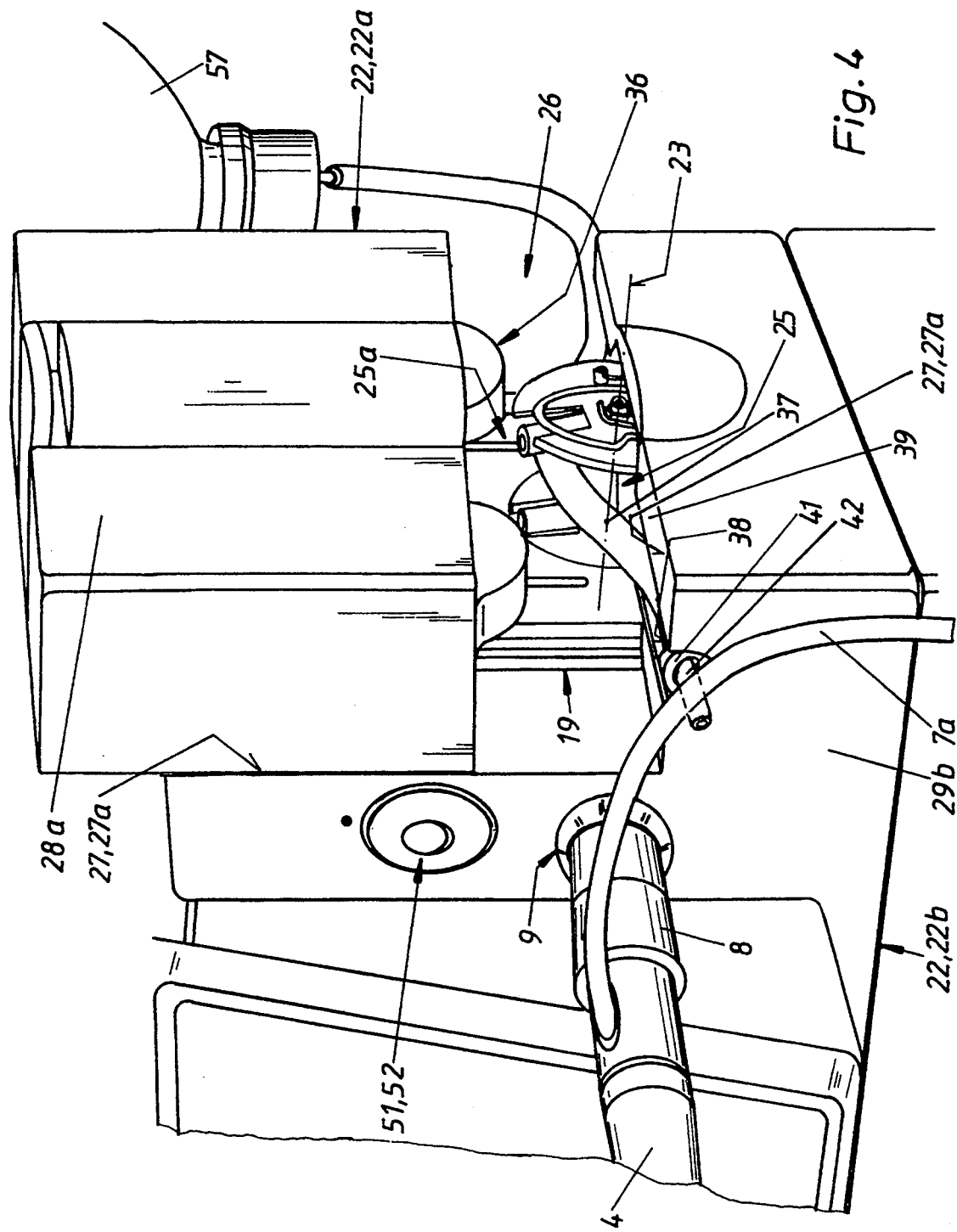

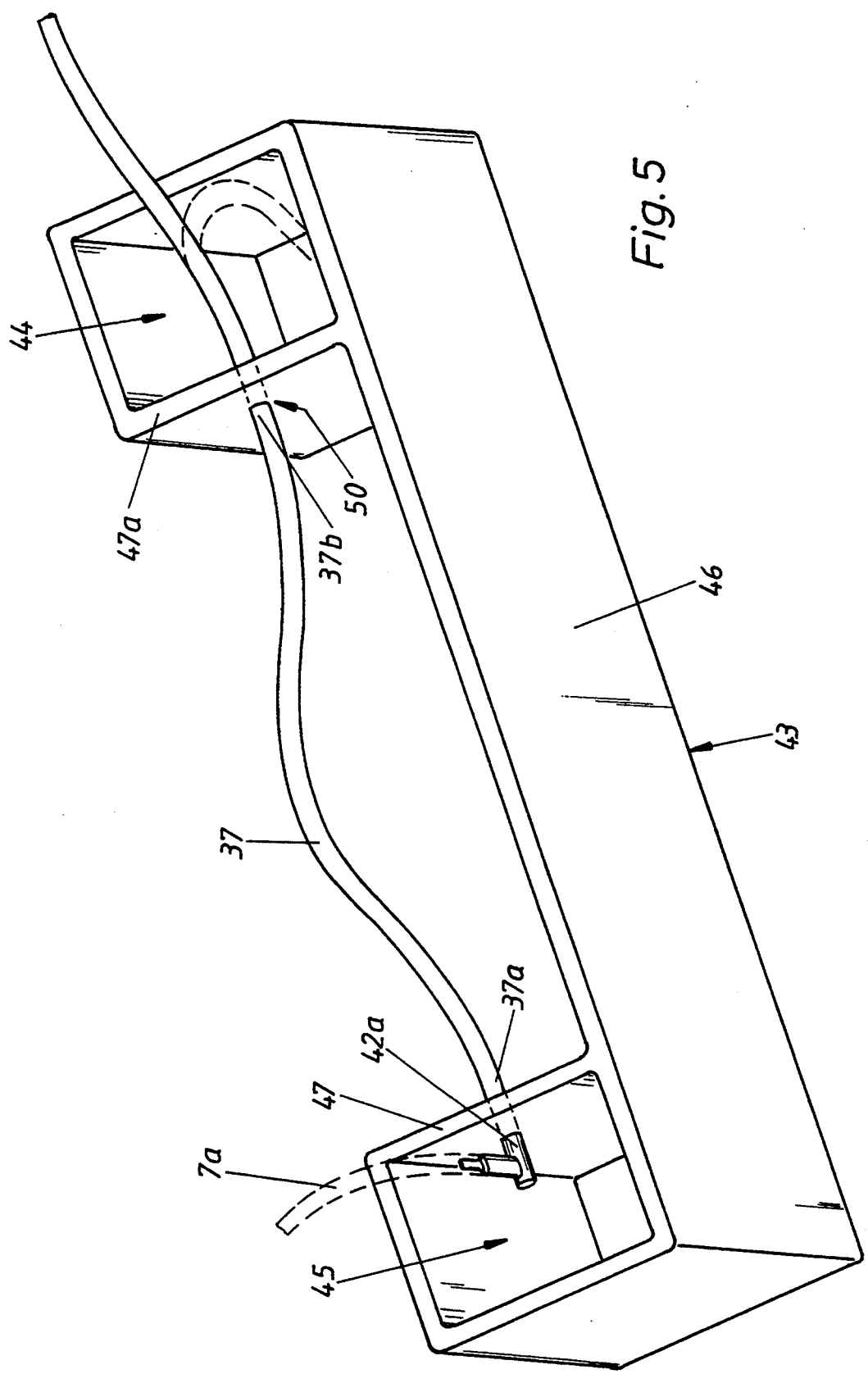

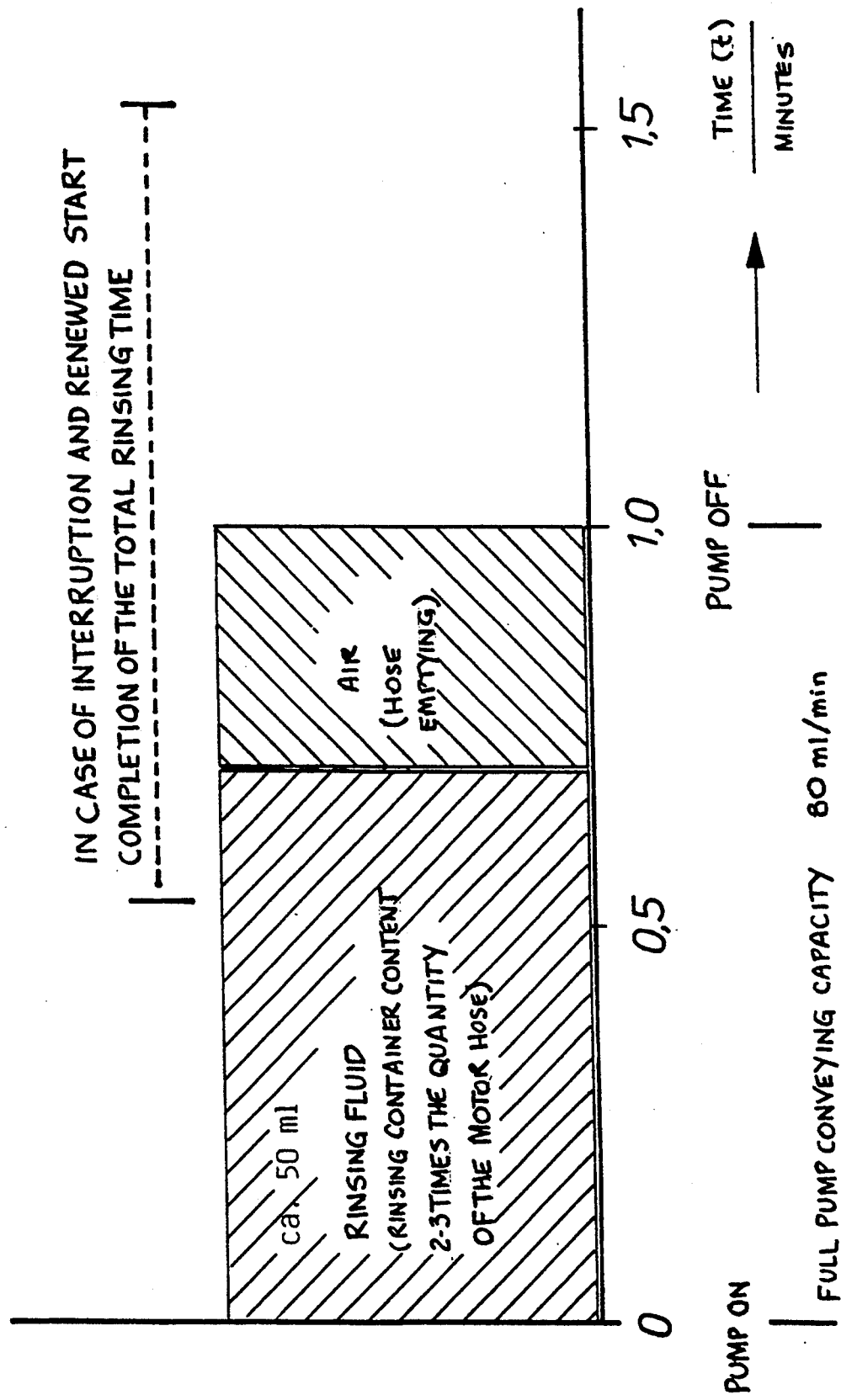

MEDICAL TREATMENT DEVICE AND METHOD FOR CLEANING A FLEXIBLE TUBE LINE

BACKGROUND OF THE INVENTION

1. Field of the Invention

The present invention relates to a medical treatment device, in particular for surgical purposes, having a supply line in the form of a flexible tube; and also relates to a method for cleaning the flexible tube.

In many instances, during the treatment of the human or animal body with a medical treatment instrument it becomes necessary to add a gaseous or, in particular, a fluid treatment agent, which can be air, water or a mixture thereof, such as in the form of a spray. Thus, especially in various instances of surgical and microsurgical treatment, it is necessary to provide a cooling fluid; in which case it is usual to employ a salt or saline solution, such as NaCl.

2. Discussion of the Prior Art

The treatment agent is conveyed to the treatment instrument through a flexible line, in particular such as a hose or flexible tube. It has already been proposed to arrange the flexible line either on or within the supply line.

In particular, when a mineral solution; for example; such as a salt solution, is used as a treatment or cooling fluid, there is then encountered the danger of possible crystallization and deposits taking place in the flexible line, which can reduce the cross-sectional flow area or even block the latter, and as a result, can impair the treatment or cooling effectiveness of the instrument. This danger becomes the greater the smaller there becomes the cross-sectional flow area of the supply line.

Heretofore, it has also already been proposed to guide the flexible hose or tube line at the end region of the supply line which is distant from the treatment instrument substantially radially out of this end region and accordingly, by by-passing a plug-in connection for the supply line, to be able to connect the flexible line to, respectively, the applicable source or pump for the treatment agent.

Accordingly, it is an object of the invention to provide a treatment device and a method of the type specified herein, through which any impairment in the supply of fluid to the treatment position is reduced or even completely eliminated.

SUMMARY OF THE INVENTION

According to the present invention there is provided a medical treatment device, in particular for surgical purposes, consisting of a treatment instrument in the shape of a handpiece which is connected to a control unit by means of a supply line. Operatively associated with the instrument, and preferably with the control unit, is a media source which, in particular, supplies a cooling fluid to the former and to which the supply line is connected through a flexible line such as a hose or tube extending located on or within the supply line. A rinsing device is adapted to be associated therewith, and which includes a source for supplying a rinsing agent and a collecting container, whereby the device can be selectively connected to the flexible line.

Pursuant to the present invention there is also provided a method for cleaning a flexible line in the form of a hose or tube for the supplying of a treatment fluid, in particular a cooling fluid, from respectively a control unit or a media source to a treatment instrument which is in the form of a handpiece of a medical treatment instrument of a medical treatment device. Herein, subsequent to a treatment or after specified or determinable time intervals, a rinsing agent is conveyed through the line, and subsequent to this rinsing, a gaseous medium, especially such as air, is conducted through the line for the purpose of scavenging the rinsing agent therefrom.

Operatively connected with the inventive treatment device is a rinsing device possessing a rinsing fluid storage container and a collecting container for spent or used rinsing agent or fluid, whereby the rinsing device can be connected to the treatment fluid feed line which is arranged within or extends on the supply line and can again be separated from the feed line in order to rinse the feed line when necessary; or selectively at regular or irregular intervals. In this connection, it is possible within the context of the invention to associate a specifically adapted pump with the rinsing device, or to also employ the pump which is already provided for feed of treatment fluid for the conveyance of the rinsing agent. In the latter instance, it is possible to connect the already provided fluid feed pump with the rinsing device or its storage container by means of switching valves which can be actuated either manually or automatically; or by re-connecting one or several line sections to the rinsing device or storage container. It is particularly advantageous to be able to automatically control the rinsing cycles in a time-dependent manner so that the person implementing the treatment need not to devote his or her attention to the rinsing procedure.

Through the method pursuant to the invention, it is possible to effectively prevent an undesirable buildup or accumulation of deposits in the feed line; or such deposits can be rinsed free and flushed out. This can be implemented in place within the treatment device, possibly automatically; in essence, the feed line does not need to be detached. In order to ensure that in the event of a subsequent treatment at the present treatment location no thrust or sudden push of rinsing agent will reach the treatment location, the feed line is evacuated after the rinsing process by conducting air therethrough.

The features incorporated in specific inventive embodiments contribute to the attainment of the objects of the invention and, moreover, lead to simple and practical developments which can be derived in a cost-effective manner, and which guarantee a dependable functioning and also a simple installation or disassembly, and concurrently ease of handling the instrument.

BRIEF DESCRIPTION OF THE DRAWINGS

The invention and further advantages which are attained thereby are now elucidated in more specific detail hereinbelow with regard to preferred exemplary embodiments, taken in conjunction with the accompanying drawings; in which:

FIG. 4 illustrates the detail of the encircled portion X in FIG. 1 with the rinsing agent container portion having been removed;

FIG. 5 illustrates the container portion of the treatment device as an individual structure shown in a perspective representation; and FIG. 6 illustrates an operational chart for the rinsing cycle.

DETAILED DESCRIPTION OF PREFERRED EMBODIMENTS OF THE INVENTION

Figure 1:
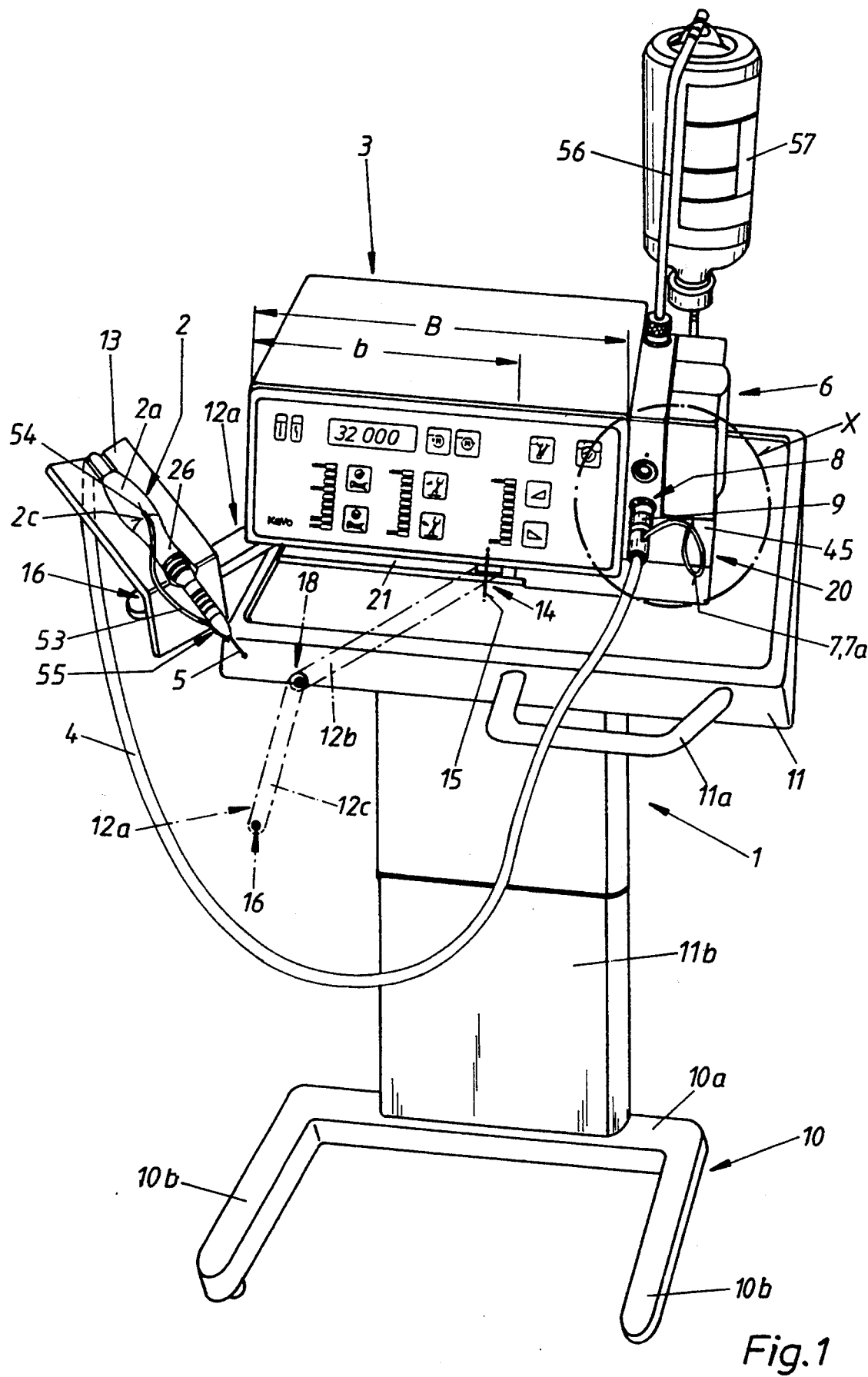
FIG. 1 illustrates a treatment device for surgical purposes constructed pursuant to the invention, shown in a front perspective representation.

The primary portions of the treatment device 1 are the provision of the treatment instrument in the form of a handpiece 2, a control unit 3 with control keys or buttons on its front side, and with an integrated electronic control device to which the handpiece 2 is connected through a bendable or flexible supply line 4. The handpiece 2 supports a treatment tool 5 at its front end, which tool 5 can be expediently selectively exchanged for different tools as required. In the case of such treatment instruments in which there is required the supplying of a coolant, especially a cooling fluid such as a salt or saline solution (NaCl) to the location of treatment, a coolant pump 6 is operatively connected with the control unit 3, wherein the coolant pump 6 can be expediently added to the control unit 3 or, alternatively, can be integrated into the unit. The coolant line 7 which leads to the front end of the handpiece 2 extends at least partially through respectively the supply line 4 and the handpiece 2. Arranged on the control unit 3 is a plug-in coupling 8 into which a plug 9, the latter of which is arranged at the free end of the supply line 4, can be plugged for the purpose of effecting a connection with the electronic control device. The control unit 3 can stand on either a frame or table 11. A holding arrangement 12 with a depository portion for the handpiece 2 when the latter is in its standby or inoperative position is preferably located on the control unit 3. In the instance of the present embodiment, a depository portion is provided in the form of a trough-shaped shell or plate 13 which is inclined obliquely towards the treatment location and on which the handpiece 2 is supported in a form-fitting manner in a position with the tool 5 pointing obliquely downwardly. The handpiece 2 is secured against lateral displacement in view of the trough-shaped form of the plate 13. The base of the trough is preferably adapted to the waisted-shape of the handpiece 2, so that a resultant form-fitting support also results in the longitudinal positional orientation of the handpiece. The plate 13 is held on a supporting arm 12a which projects away from the table 11 or from the housing of the control unit 3 in an approximately horizontal orientation, and is freely pivotable at the end of the arm 12a through preferably a pivot joint about an approximately vertical swivel axis.

The table 11 stands on the ground supported on suitable rollers (not shown) and can be displaced by gripping it manually, preferably at a handle 11a on the front side thereof. The table 11 is supported on the upper end of a supporting column 11b which stands on the crosspiece portion 10a of a U-shaped standing frame 10, the leg portions 10b of which point towards the operating side.

The supporting arm 12a is variable in terms of its length and is connected by a pivot joint 12 with the control unit 3 at the end which is distant from the holding arrangement 12 so as to be pivotable about a vertical swivel axis 15. Due to this features, the holding arrangement 12 together with the handpiece 2 can not only be swung freely horizontally, but can also be adjusted with regard to its distance from the control unit 3. As a result, it is freely adjustable over a wide range of movements and can be set into selected stand-by or idle positions which are expedient with regard to the treatment location or the treatment position, and in which the person implementing the treatment can grip the handpiece with ease of handling and then again deposit the handpiece. In the drawing, the supporting arm 12 is represented by phantom lines in its outwardly extended position. In the instance of this schematic representation, the holding arrangement 12 is omitted for purposes of clarity in order to show the pivot joint 16 supporting the arrangement at the free end of the supporting arm 12a, whereby the joint 16 can be formed by the provision of a vertical bore hole into which a round peg (not shown) projecting downwardly from the holding arrangement 12 can be inserted from above while providing play to enable movement.

Within the context of the invention, the supporting arm 12a can be a telescopable supporting arm. In the instance of the present embodiment, the supporting arm 12a is formed in the sense of an articulated lever with two supporting arm portions 12b, 12c which are connected with each other at their facing ends by a central pivot joint 18 having a vertical swivel axis. The two interconnected ends of the supporting arm portions 12b, 12c preferably file one on top of the other, in which case they overlap and a joint pin is extended through them positioned in vertical bores. It is advantageous, on the one hand, in view of savings in space and, on the other hand, for the attaining of an adequate stability, to produce the supporting arm portions 12b, 12c from planar strips each of rectangular cross-section, and which are arranged in a planar manner.

In the case of the present invention, a horizontal recess 21 is provided in the lower region of the box-shaped control unit, shown in this embodiment below the control or keyboard panel, into which recess there can be swung the supporting arm 12a. In this connection, the joint 14 can be arranged in the region of the front side of the control unit 3 or within the recess 21, as represented in the drawing. In the present instance, the recess 21 is arranged in the front left corner region of the control unit 3, and is accessible or open on the operating side, in effect, both from the front and from the left side. The width b of the recess 21 which extends from the left side of the control unit 3 towards the right corresponds with substantially three quarters of the width B of the control unit 3, so that the recess 21 ends at a distance from the right side of the control unit 3. In the swung-in position, the plate 13 is located directly in front of the right half of the front side of the control unit 3. The height of the recess 21 is dimensioned to be so large that the supporting arm 12a can be swung in while providing vertical play for allowing movement.

The width b of the recess 21 and the length of the inner supporting arm portion 12b are preferably correlated with each other in such a manner that, in the swung-in position according to FIG. 1, the inner supporting arm portion 12b or the central joint 18 do not project laterally out of the recess 21.

The recess 21 is preferably formed in a support which in particular is plate-shaped, in this instance in a base plate 3a of the box-shaped control unit 3. The base plate 3a can be detachably secured to the control unit 3; for example, by means of screws. The arrangement or the control unit 3 can, respectively, be completed in a modular manner by means of the base plate 3a which can be added, when applicable in conjunction with the holding arrangement 12, or be selectively retrofitted thereto.

The previously described configuration and features of the holding arrangement 12 renders possible selective setting of the stand-by position of the handpiece 2 in the entire front region of the control unit 3. The stand-by position of the holding arrangement 12 which is to be selected can thus be adapted to a plurality of potentially also difficult treatment positions.

In the case of the present instance, the pump 6 is formed by means of a hose pump which is arranged in the substantially box-shaped housing 22 of the control unit 3. The housing portion accommodating the hose pump 6 can also be an add-on housing which supplements the housing 22. Pursuant to the invention, the hose pump 6 is arranged in the right end region of the housing 22 at substantially mid-height, in which event the axis of rotation 23 of the hose pump 6 extends horizontally and in parallel with the operating side 24 of the control unit 3 and, in a side view from the right, the hose pump 6 is arranged substantially in the center within the housing 22.

Figure 2:
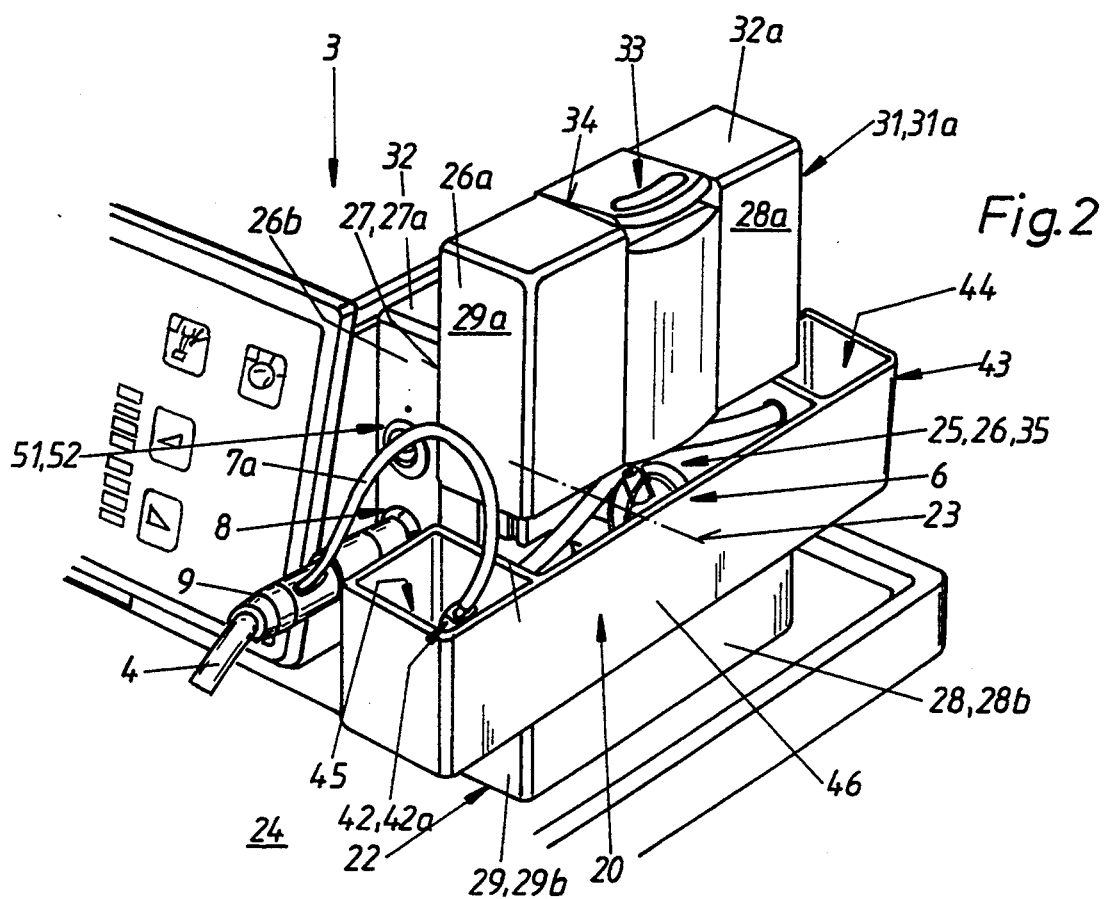
FIG. 2 illustrates the detail of the encircled portion X in FIG. 1, shown in an enlarged representation.
Figure 3:
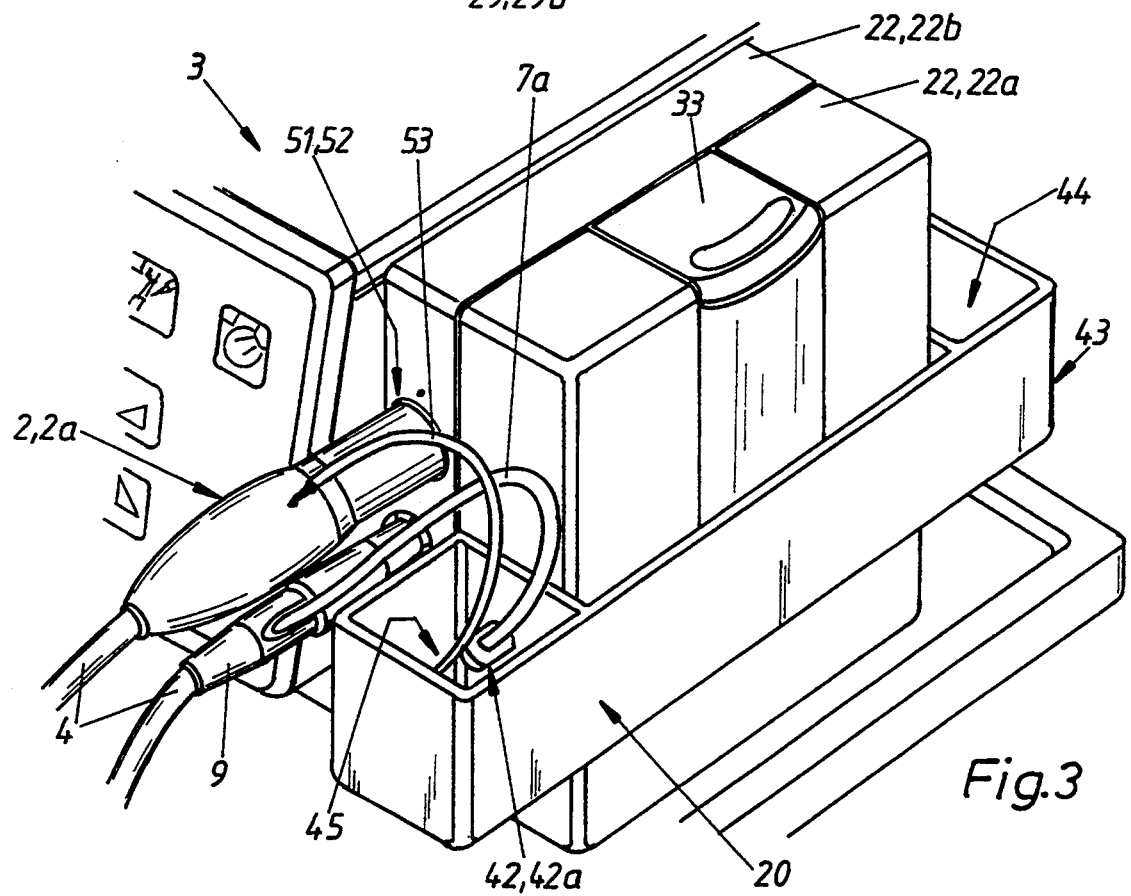
FIG. 3 illustrates the detail of encircled portion X in FIG. 1 in another functional disposition.

The accessibility to the pump space 25 of the hose pump 6 is ensured by a housing opening 26 which can be opened by the upward displacement of a housing portion 22a and can be closed again by the downward displacement of that housing portion. The housing portion 22a is separated from the other housing portion 26b by means of an angular dividing joint 27 possessing planar dividing joint sections 27a, 27b, with the dividing joint section 27a ending towards the top being preferably extended vertically, and with the dividing joint section 27b extending horizontally from the first dividing joint section 27a substantially at the level of the axis of rotation 23 and ending in the applicable side wall 28 which is shown at the right. The dividing joint sections extend from the front; in effect, viewed from the operating side 24, passing through the housing from the front wall 29 thereof as far as the rear wall 31. The housing portion 22a is thereby located in the upper right corner region of the housing 22 and comprises a side wall portion 28a, a front wall portion 29a, a cover wall portion 32a of the cover wall 32 of the housing 22 and a rear wall portion 31a. The housing portion 22a is displaceable preferably vertically in a guide 19, which is only represented in FIG. 4 and which is arranged between this portion and the other stationary housing portion 22b, so as to be positionable between the open position shown in FIG. 2 and the closed position shown in FIG. 3, and can be positioned in each of the respective end positions. The housing portion 22a is preferably prestressed by means of a spring into its upper open position, and can be engaged in its lower closed position by means of a therewith integrated, releasable locking arrangement. In the case of the present embodiment, a press key 33 is used for this purpose, bordering against the upper side of the cover wall portion 32a, arranged in a recess 34 arranged in the upper region of the housing portion 22a approximately substituting the housing contour and being pivoted about a horizontal swivel axis which extends at right angles to the axis of rotation 23; in essence, such that it can be tilted towards the right side in a joint which is integrated in the housing portion 22a. The above-described locking arrangement is released by manual pressure exerted against the push button 33, with the push button or toggle swinging or tilting towards the side. For closing purposes, the housing portion 22a is to be pressed down manually until the locking arrangement automatically engages in the closed position.

The pump portions of the hose pump 6 are of a type known per se, and are formed by means of a rotor 35 which can be driven by a motor (not shown) and which is equipped with diametrically opposed squeeze rollers and lateral guide rollers, and an abutment 36 which cooperates therewith (FIG. 4). The abutment is formed in an undulating shape with fork-shaped abutment extensions and laterally engages over the rotor 35 from above. The vertical plane containing the vertical dividing joint section 27a is located at about the inner end of the rotor 35. The horizontal plane containing the horizontal dividing joint section 27b lies at about the level of the axis of rotation 23 (FIG. 4). The pump hose 37 of the hose pump, with housing portion 22a opened, can be easily and conveniently inserted from the side into the working space 25a, which is similarly open and is located between the rotor 35 and the abutment 36, so that the hose extends in a curved manner over the rotor 35. The end regions of the pump hose 37 are recessed in slots 38 in the dividing joint section 27b which extend transversely to the axis of rotation 23 and are located in wall portions 39 of the stationary housing portion 28b bordering against the upper side by the dividing joint section 27b. In the side wall portions 29b of the stationary housing portion 22b there are formed lead-through holes 41 for the pump hose 37, which are in alignment with the slots 38 and which end towards the top, in which case, in the lead-through hole 41 on the front side, a connection fitting 42 which is connected with the pump hose 37 is inserted from above and is held in a non-displaceable and form-fitting manner in the longitudinal direction of the pump hose 37 by engagement into a groove in the lead-through hole 41 extending in the longitudinal direction of the pump hose 37.

A rinsing agent container portion 43, which is not illustrated in FIG. 4 for the purpose of clarifying the overall view, has a rinsing agent storage container 44 and a collecting container 45 for used or spent rinsing agent. These containers 44, 45 are formed on a vertical connecting wall 46, preferably integrally therewith, so that they project to one wide side of the connecting wall 46. The spacing of the containers 44, 45 from each other is adapted to the width of the housing 22 extending transversely of the operating side 24 so that the rinsing agent container portion 43 can be added horizontally to the right end face of the housing 22 from the side, such that the containers 44, 45 overlap the housing 22 on the front side and on the rear side respectively. The width of the containers 44, 45 extending in parallel with the operating side 24 is preferably correlated with the corresponding width of the movable housing portion 22a. For the purpose of holding the rinsing agent container portion 43 in this added-on position in which it projects somewhat upwardly above the horizontal dividing joint section 27a, the rinsing agent container portion 43 is held or secured in a detachable manner to the stationary housing portion 22b by suitable means which are not illustrated; for example, such as extensions on the stationary housing portion 22b engaging therebeneath. In this regard, the connection fitting 42 is also set through the inner wall 47 of the collecting container 45, which lies opposite thereto, in a hole with the maintenance of a seal through the provision of a sealing ring or the like. The connection fitting 42 can also be just seated in the inner wall 47 in the collecting container 45; for example, by being screwed therein, preferably in the form of an angular fitting 42a. A hole 50 for the pump hose 37 is provided in the opposite inner wall 47a in alignment with the rear lead-through hole 41. The connection to the hose 7a which is guided radially out of the supply line 4 is created by respectively connecting the hose to either of the connection fittings 42 or 42a. The pump hose 37 is sealed in the hole 50, or the hole 50 is located above the filling level in the storage container 44.

FIG. 5 shows the rinsing agent container portion 43 as a detachably arranged add-on portion which is held on the housing 22b in the context of a plug-in fitting in that the pump hose sections 37a, 37b which are present on the inside on the inner walls 47, 47a are set into the lead-through holes 41. The container portion 43 can thus be removed and installed with ease by being hooked therein; for example, for the purpose of facilitating emptying the collecting container 45. In the case of a separate rinsing agent container portion 43 which can be selectively added on, a specific pump hose 37c is preferably associated with the portion 43 so that it is not necessary to connect the pump hose with the connection fitting 42a and thread it through the hole 50. In the instance of such an embodiment, before adding the rinsing agent container 43 with the pump hose 37c, there must be removed the pump hose 37.

The connection to the hose 7a which is guided radially out of the supply line 4 is produced by its attachment to the connection fitting.

Close to the collecting container 45 arranged at the front on the housing 22, preferably above the plug-in coupling 8 which is arranged adjacent to container on the left, a parking position in the form of a holding arrangement 51 for the handpiece 2 is provided on the control unit 3 or, respectively, its housing 22. The holding arrangement 51 can be formed by means of a plug-in arrangement into which the handpiece 2 can be inserted or connected. In the present case, the holding arrangement 51 is formed by means of a horizontal hole 52 on the front side of the control unit 3 into which the handpiece 2 or a portion of the latter can be plugged or connected. Hereby, the handpiece consists of two handpiece portions which are arranged one behind the other, and can be interconnected by means of a rapid-action coupling or plug-in fitting, this being essentially a rear handpiece portion 2a connected with the supply line 4 and a front handpiece portion 2b which supports the treatment tool 5. In this connection, the arrangement is such that the rear handpiece portion 2a, subsequent to its separation from the front handpiece portion 2b, can be plugged into the hole 52.

In the case of the present two-piece handpiece 2, the coolant line 7 bridges the dividing joint 2c of the handpiece 2 on the outside thereof. For this purpose, there is provided a hose section 53, the ends of which are connected to connection fittings 54, 55 which are arranged on the rear handpiece portion 2a and front handpiece portion 2b extending from the applicable coolant line 7. The distance of respectively the parking position or holding arrangement 51 from the collecting container 45 is only so large, or the hose section is so long, that in the position of the handpiece 2 assumed in the holding arrangement 51, the hose section 53 can be hooked into the collecting container 45. A rinsing process can be undertaken in this position. In the event the arrangement was previously set up for the feed of coolant, the pump hose 37c must be separated from the present coolant storage container 57 which is suspended on a carrier rod 56 on the control unit 3 and which can be closed by releasing the existing connection and must be plugged with its free end into the rinsing agent storage container 44. The rinsing process can then take place with the rinsing device 20 by being initiated; for example, through actuation of an actuating element located on the control keyboard. A cut-off arrangement for the rinsing process is preferably operatively associated with the control unit 3, and automatically terminates the process after a predeterminable period of time. The quantity of rinsing agent which is thereby suctioned by the hose pump 6 out of the rinsing agent storage container 44 and conveyed further should, preferably, correspond to approximately two to three times the total volume of the pump hose 37c or the rinsing agent line. The rinsing agent, preferably water which is flushed through, is introduced into the collecting container 45 by means of the hose section 53. When flushing through, deposits or crystals of the salt solution which are present in the coolant line 7 are rinsed free and flushed away. As a result, there is prevented any impairment of the through-flow cross-sectional area of the coolant line 7, and thus as well any deterioration in the cooling.

Within the scope of the invention it is also possible to employ the holding arrangement 12 in order to hold the handpiece 2 in the parking position. This is possible because the holding arrangement 12 can be swung due to the horizontal mobility of the holding arm 12a until it is close to the collecting container 45. When the holding arrangement 12 is used, the handpiece 2 does not need to be removed if the holding arrangement 12 can be swung so far towards the collecting container 45 that the free end of the handpiece 2 extends together with the present coolant outlet into the collecting container 45.

At the end of the rinsing cycle, the pump hose 37c must then be re-connected with its rear end to the coolant storage container 57.

As shown by FIG. 6 illustrating a rinsing agent cycle, preferably only air is introduced at the end of the rinsing procedure in order to displace the rinsing agent from the feed line 7. The air volume preferably amounts to approximately 1/5 to ½, in particular approximately ⅓, of the volume of the rinsing agent, but is greater than the volume in the feed line 7 in order to be able to displace the rinsing agent present therein. In order to terminate the flow of rinsing agent, the pump hose 37c must therefore be removed from the storage container 44, or the storage container 44 must be dimensioned to be so large or is to be filled such that the pump hose 37 aspirates air after the rinsing agent has been conducted out. In the case of effectuating a control with valves, it is possible to connect or open an air suction line.

In the case of the present instance, the rinsing process takes a total time of approximately 1 minute. The present control is preferably designed in such a manner that in the event the rinsing process is interrupted, the latter is again turned on and runs in its entirety; there is; in effect, a conveyance of rinsing agent and of air.

The invention also comprises an expedient rinsing method.

I claim:

1. In a method for the cleaning of a supply line conveying a treatment fluid to a treatment instrument including a handpiece connected to a control unit through said supply line; and a media source for supplying said fluid and for reusing said fluid from said treatment fluid supply line; the improvement comprising:
 a) conveying a liquid rinsing agent through said supply line upon selective completion of a treatment at predetermined time intervals; and
 b) conveying a gaseous medium through said supply line subsequent to discharge of said liquid rinsing agent therefrom so as to scavenge residual rinsing agent from said supply line.

2. A method as claimed in claim 1, wherein said handpiece is positioned proximate a collecting container during the conveyance of said rinsing agent through said supply line, and said spent rinsing agent is discharged into said collecting container.

3. A method as claimed in claim 1, wherein said treatment fluid is a cooling fluid.

4. A medical treatment device for the cleaning of a supply line conveying a treatment fluid to a treatment instrument in the form of a handpiece; a control unit connecting said supply line to said treatment instrument; rinsing means including a source for supplying a rinsing agent and a collecting container for said rinsing agent, said rinsing means being located in said treatment device; a flexible line connected to said control unit and to said supply line for the selective connection with said rinsing agent source and a source for a gaseous medium so as to ensure said pressure medium to scavenge residual rinsing spent from said supply line at the termination of a rinsing process for cleaning said supply line.

5. A treatment device as claimed in claim 4, wherein said rinsing agent means is connectable to the flexible line by an actuation of electrical control elements.

6. A treatment device as claimed in claim 4, wherein said rinsing agent means includes a rinsing agent storage container and a pump for conveying said rinsing agent.

7. A treatment device as claimed in claim 4, wherein a common pump is provided for effecting the treatment agent feed and the rinsing agent feed.

8. A treatment device as claimed in claim 4, wherein said collecting container is arranged in a front region of the control unit.

9. A treatment device as claimed in claim 4, wherein a holding device for said handpiece is arranged on a front side of the control unit.

10. A treatment device as claimed in claim 9, wherein said holding device comprises a receiving hole into which there is insertable at least a portion of the handpiece.

11. A treatment device as claimed in claim 9, wherein said holding device comprises a receiving trough for depositing said handpiece thereon.

12. A treatment device as claimed in claim 9, wherein said gaseous medium comprises pressurized air.

* * * * *